(12) United States Patent
Jadidi et al.

(10) Patent No.: US 9,554,722 B2
(45) Date of Patent: Jan. 31, 2017

(54) ELECTRODE CONNECTION MONITORING

(71) Applicant: Sunstar Suisse SA, Etoy (CH)

(72) Inventors: Faramarz Jadidi, Hasselager (DK); Claus Steen, Silkeborg (DK)

(73) Assignee: Sunstar Suisse SA, Etoy (CH)

(*) Notice: Subject to any disclaimer, the term of this patent is extended or adjusted under 35 U.S.C. 154(b) by 76 days.

(21) Appl. No.: 14/574,503

(22) Filed: Dec. 18, 2014

(65) Prior Publication Data

US 2015/0105685 A1 Apr. 16, 2015

Related U.S. Application Data

(63) Continuation of application No. 12/679,051, filed as application No. PCT/DK2008/050231 on Sep. 22, 2008, now abandoned.

(30) Foreign Application Priority Data

Sep. 21, 2007 (GB) .................................. 0718486.4
Sep. 21, 2007 (GB) .................................. 0718487.2

(51) Int. Cl.
| | | |
|---|---|---|
| A61B 5/04 | (2006.01) | |
| A61B 5/0488 | (2006.01) | |
| A61B 5/00 | (2006.01) | |
| A61N 1/36 | (2006.01) | |
| A61B 5/11 | (2006.01) | |
| A61B 5/0424 | (2006.01) | |
| A61N 1/08 | (2006.01) | |

(52) U.S. Cl.
CPC ........... *A61B 5/0488* (2013.01); *A61B 5/1104* (2013.01); *A61B 5/4557* (2013.01); *A61B 5/486* (2013.01); *A61B 5/6843* (2013.01); *A61N 1/36014* (2013.01); *A61B 5/0424* (2013.01); *A61B 5/7257* (2013.01); *A61N 2001/083* (2013.01)

(58) Field of Classification Search
CPC ... A61B 5/0488; A61B 5/0424; A61B 5/4577; A61B 5/486; A61B 5/6843; A61B 5/7257; A61N 1/36014; A61N 2001/083
See application file for complete search history.

(56) References Cited

U.S. PATENT DOCUMENTS

| | | | |
|---|---|---|---|
| 4,233,987 A | 11/1980 | Feingold | |
| 4,669,477 A | 6/1987 | Ober | |
| 4,715,367 A | 12/1987 | Crossley | |
| 5,772,591 A | 6/1998 | Cram | |
| 6,076,011 A | 6/2000 | Hoover | |

(Continued)

FOREIGN PATENT DOCUMENTS

WO WO-2004/087258 A1 10/2004

OTHER PUBLICATIONS

U.S. Appl. No. 12/679,051, filed Jan. 13, 2011.

*Primary Examiner* — Devin Henson
(74) *Attorney, Agent, or Firm* — Dinsmore & Shohl LLP; Douglas Wathen

(57) ABSTRACT

The present invention relates to an apparatus and a method for measuring muscular activity, in particular in relation to bruxism, and providing an electrical stimulation in response to the measured muscular activity through electrodes applied to the skin of an individual, wherein the quality of the connectivity of the electrodes to the skin is monitored and the electrical stimulation signal is changed based on said quality measurement.

23 Claims, 2 Drawing Sheets

(56) References Cited

U.S. PATENT DOCUMENTS

| | | | |
|---|---|---|---|
| 6,270,466 B1* | 8/2001 | Weinstein | A61B 5/0488 600/590 |
| 6,638,241 B2 | 10/2003 | Yerushalmy | |
| 7,130,673 B2 | 10/2006 | Tolvanen-Laakso et al. | |
| 7,340,294 B2* | 3/2008 | Gray | A61B 5/0424 600/509 |
| 8,160,689 B2 | 4/2012 | Jadidi | |
| 2006/0184059 A1* | 8/2006 | Jadidi | A61B 5/04015 600/546 |

* cited by examiner

ELECTRODE CONNECTION MONITORING

CROSS-REFERENCE TO RELATED APPLICATIONS

This application is a continuation of U.S. patent application Ser. No. 12/679,051, filed Mar. 19, 2010, which is the U.S. national phase of PCT/DK08/50231, filed Sep. 22, 2008. Said U.S. national phase PCT/DK08/50231, filed Sep. 22, 2008 claims priority to GB0718487.2, filed Sep. 21, 2007, and GB0718486.4, filed Sep. 21, 2007, the contents of all of which are incorporated herein in their entirety.

FIELD OF THE INVENTION

The present invention relates to an apparatus and a method for use in analysing EMG signals. The apparatus provides for monitoring the quality of the connection of EMG electrodes to the source of said signals, which is normally the skin.

BACKGROUND OF THE INVENTION

In conducting the measurement of EMG signals, electrodes are placed or adhered onto the skin, usually with a layer of electrically conducting gel between the skin surface and the electrode proper. The quality of the signals received will depend on the quality of the connection made between the skin and the electrode, and this may not be easy for the user to ascertain. If the connection is poor, the sensing of particular signals may fail and actions that should be triggered in response to particular conditions may not take place. In Functional Electrical Stimulation systems, electric currents are impressed on the skin by voltage applied via skin electrodes either to produce a muscular reaction or to provide a sensory input. If the connection between the electrode and the skin is poor, this can lead to excessive voltage being applied or can lead to a failure to produce the desired effect.

For instance, in WO2004/087258, episodes of bruxism are detected by monitoring EMG signals received from electrodes on the skin of a user and when such an episode is detected, an mild electric shock is applied via the electrodes as a biofeedback signal. In order that the apparatus can function correctly to detect the bruxism episodes and also to apply the biofeedback signal safely, a good connection between the skin and the electrodes is required. It is described that the connection can be checked by applying a voltage between a pair of the electrodes to be tested, so as to produce a predetermined current, and measuring the voltage required, and further that the user is informed, in case of reduced connection, to adjust the apparatus, such as the strap pressing the electrodes to the skin.

All patent and non-patent references cited in the application, or in the present application, are also hereby incorporated by reference in their entirety.

SUMMARY OF THE INVENTION

The present invention relates to an apparatus and a method for measuring muscular activity, in particular in relation to bruxism, and providing an electrical stimulation in response to the measured muscular activity through electrodes applied to the skin of an individual, wherein the quality of the connectivity of the electrodes to the skin is monitored and the electrical stimulation signal is changed based on said quality measurement.

Accordingly, in a first aspect the invention relates to an apparatus comprising electrodes adapted for being applied to the skin of an individual, wherein the apparatus is adapted for receiving and monitoring electrical signals and comprises respective inputs for receiving signals from at least a first electrode of said electrodes and a reference electrode, and for providing electrical stimulation to said individual, said apparatus comprising:

means for measuring EMG signals from said electrode(s) when the electrodes are applied to the skin, a source of a monitoring signal having a frequency, an output for use in applying said monitoring signal to said at least first electrode, means for determining the received signal of said frequency of the monitoring signal in signals received at said inputs, means for providing an electrical stimulation feedback signal upon the detection of EMG signals indicative of a muscular activity of the individual, wherein the received signal of said frequency of the monitoring signal in signals received at said inputs is measured for monitoring the quality of the electrical connection between the electrodes and the skin, and the feedback signal is modulated if the quality of the electrical connection between the electrodes is changed.

Furthermore, the present invention provides a method for monitoring the electrode connection, wherein the incoming signals relating to the monitoring signals are analysed by a Fourier transform analyser. Accordingly, in a second aspect the invention relates to an apparatus for receiving and monitoring electrical signals comprising respective inputs for receiving signals from at least a first electrode and a reference electrode, a Fourier transform analyser for extracting frequency content information from said signals, a source of a monitoring signal having a frequency, an output for use in applying said monitoring signal to a said electrode, and means for determining the amplitude of the said frequency of the monitoring signal in signals received at said inputs as determined by said Fourier transform analyser.

In yet another aspect the invention relates to a method for ameliorating and/or treating bruxism by applying electrodes as described above to the skin above a facial muscle of said individual, preferably the masseter muscle or the temporalis muscle, applying a stimulating signal, should a bruxism event happen, and monitoring the connection between the electrodes and the skin. Accordingly, the invention relates to A method for monitoring activity of the temporal muscle and/or the masseter muscle, in particular activity due to teeth and/or jaw clenching, said method comprising the steps of:

measuring EMG signals from said electrode(s) when the electrodes are applied to the skin, applying a monitoring signal having a frequency to said at least first electrode, determining the received signal of said frequency of the monitoring signal in signals received, for monitoring the quality of the electrical connection between the electrodes and the skin, providing an electrical stimulation feedback signal upon the detection of EMG signals indicative of a muscular activity of the individual, wherein the feedback signal is modulated if the quality of the electrical connection between the electrodes is changed.

Furthermore, the invention relates to a method for monitoring electrode connections, by receiving and monitoring electrical signals from at least a first electrode and a reference electrode, extracting frequency content information from said signals and performing a Fourier transform analysis, applying said monitoring signal to a said electrode, and determining the amplitude of the said frequency of the monitoring signal in signals received as determined by said Fourier transform analyser.

DETAILED DESCRIPTION OF THE INVENTION

Figure 1:
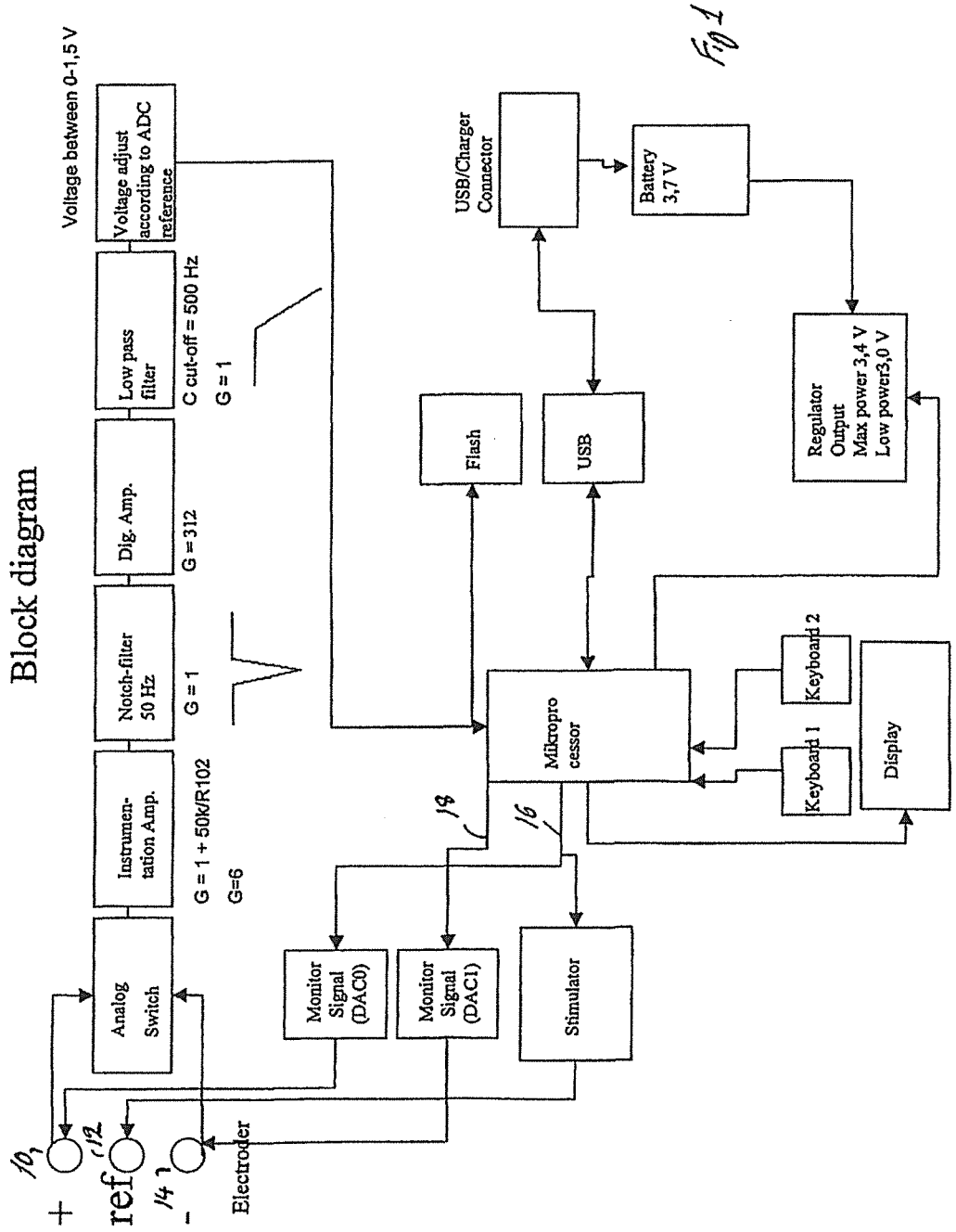
FIG. 1 shows a block circuit diagram for a bruxism monitoring apparatus of the kind described in WO2004/087258 but modified to incorporate electrode connection monitoring according to the present invention.

As described above the apparatus according to the invention has electrodes adapted for being applied to the skin of an individual for measuring EMG as a measure for muscular activity, in particular in relation to bruxism, and providing an electrical stimulation in response to the measured muscular activity through the electrodes. The apparatus is in particular useful for measuring muscular activity relating to bruxism during night when the individual is at sleep. Accordingly, the electrodes are applied to the skin before the individual goes to bed and must stay on the skin during the sleep until next morning in order to be effective. The connection of the electrodes may be of good quality at the start of the sleep, however due to changes in for example temperature, pressure and general movements of the individual the quality of the connection may be reduced during the sleep. Thus, the present invention provides an apparatus wherein the quality of the connection may be monitored during use of the apparatus, and furthermore, that the electrical feedback stimulation signal may be changed due to changes in the connection, in order to reduce harm to the individual and maintain efficiency of the apparatus, at least to some degree.

It will be appreciated that the electrodes may each comprise a solid conductive electrode member provided with a respective patch of conductive gel in an assembly, in which case it will be the area of the gel that defines the contact area of the electrode rather than the size of the electrode member. However, even when a gel is used the connection between electrode and skin may vary depending on a variety of factors, such as described above. The area of an electrode member in contact with such a gel patch may be approximately from 5% to 100% of the electrode contact area (i.e. the gel patch area), in some cases 25% to 75%, e.g. about 50%.

The electrode contact areas may extend along or on a said line a distance of from 1 to 10 mm from one side to an opposite side of the electrode contact area and may extend transversely of a said line by a distance of from 1 to 10 mm from one side to an opposite side of the electrode contact area, the maximum distance along said line from an edge of a first said electrode contact area to an opposite edge of the furthest away of the other two electrode contact areas being not more than 60 mm, more preferably 50 mm. Preferably, the contact areas of the electrodes may extend along or on said line a distance of from 3 to 7 mm from one side to an opposite side of the electrode contact area. Similarly, the contact areas of the electrodes may extend transversely of said line by a distance of from 3 to 7 mm from one side to an opposite side of the electrode contact area.

Thus, for instance the electrode contact areas may be circular and of diameter from 2-20 mm, more preferably from 5-15 mm, e.g. about 10 mm, and the electrode members may also be circular having a diameter of from 1-10 mm, more preferably from 3 to 7 mm, e.g. about 5 mm. The electrode contact areas and the electrode members may be of other shapes having equivalent areas to those described above.

Preferably, the apparatus comprises respective inputs for receiving signals from said first electrode, from a second electrode and from said reference electrode. Preferably, there are inputs for just the three electrodes, although more may be provided. Preferably, there are respective outputs for applying said monitoring signal to each of the first electrode and the second electrode.

The apparatus preferably further comprises respective electrodes connected to said inputs and to said output(s).

Preferably, the apparatus further comprises circuit means adapted to provide a preset monitoring signal current between said first electrode and said reference electrode, and optionally also circuit means adapted to provide a preset monitoring signal current between said second electrode and said reference electrode. The means for determining the received signal of said frequency, may be provided to determine and optionally to record the voltage amplitude of said monitoring signal required to achieve said preset current level between said electrode pair(s). Thus, the quality of the connection between the electrodes through a material to which they are connected may be determined.

Said electrodes are preferably provided in an electrode assembly in which said electrode assembly comprises two or more preferably three electrodes mounted on a common substrate in a fixed spatial relationship one to another. Said electrode assembly is preferably adapted to be applied to the skin above the masseter or temporalis muscles, i.e. of a shape adapted to follow the facial contours most generally met at the various individuals to be treated.

Preferably, where first, second and reference electrodes are provided, said reference electrode lies approximately equidistant from said first and second electrodes.

The apparatus may comprise means for measuring the amplitude within the received signals of at least one selected frequency other than that of said monitoring signal.

In a preferred aspect of the practise of the invention, said apparatus is for measuring EMG signals from said electrodes when the electrodes are applied to the skin and the amplitude of the said frequency of the monitoring signal in signals received at said inputs as determined by said Fourier transform analyser is measured for monitoring the quality of the electrical connection between the electrodes and the skin.

Preferably, the apparatus is for functional electrical stimulation (FES). In some FES devices, electrical stimulating pulses are delivered via skin mounted electrodes to activate muscle functions. In such devices it will be desirable to be able to monitor the connection to the skin of the electrodes by the use of apparatus according to the invention. However, apparatus according to the invention preferably also comprises means for the detection of EMG signals and means for providing a feedback signal upon the detection of EMG signals indicative of a muscular activity.

In particular, said activity may be an episode of bruxism.

In order that the stimulation signal has the desired effect on bruxism behaviour and yet does not wake the user from sleep, or is adjustable to achieve these ends, a match is needed between the form of the signal and the form of the electrode assembly. For use with the electrode assembly conformations described herein, it is preferred that said electrical stimulation signal is a biphasic signal which is initiated at a voltage applied to the electrode assembly of not more than 10 volts peak to peak and is raised to a maximum peak to peak voltage at a rate of not more than 500 V/sec, said signal having a duration of not more than 2 sec, a said maximum voltage of not more than 100 volts peak to peak.

Preferably, said biphasic signal has a pulse width of from 50 μsec to 10 msec, more preferably from 50 to 500 μsec, more preferably from 100 to 300 μsec, for instance about 150 μsec.

The signal is preferably initiated at a voltage applied to the electrode assembly of not more than 5 volts peak to peak. The signal preferably increases in intensity from its initial value at a rate of not more than 350 V/sec, more preferably not more than 250 V/sec, for instance between 100 and 250 V/sec, e.g. about 200V/sec.

The duty cycle of the signal may be from 1 to 99%, but is preferably in the range of from 30 to 70%, suitably about 50%.

The frequencies of muscle activity are normally in the range of from 0 to about 350 Hz, whereas the frequencies of bruxism related muscle activity is normally found in the range of from 250-350 Hz, more specifically from 268-332 Hz. The frequency of the monitoring signal is preferably different from the frequencies of muscle activity, and more preferably the frequency of the monitoring signal is higher than the frequencies of muscle activity. Accordingly, the frequency of the monitoring signal is preferably above 350 Hz, more preferably above 400 Hz, more preferably above 450 Hz, more preferably above 500 Hz, and even more preferably about 600 Hz.

Preferably, said EMG signals indicative of the muscular activity are identified by measuring therein the amplitude of one or more selected frequencies different from the frequency of the monitoring signal. The measured frequency or frequencies may be selected for maximal differentiation between bruxism activity and possibly confounding muscular activities such as changes in facial expression, e.g. grimacing, and they may be selected to best suit detection of bruxism in an individual user. Apparatus to which the invention may be applied is described in WO 2004/087258.

If the quality of the connection between the electrode(s) and the skin is reduced, it is preferred that the electrical stimulation signal is changed based on said quality measurement. For example, if the determination of the received signal of said frequency of the monitoring signal implies a poor connection between then it is preferred that the feedback stimulation signal is reduced, such as wherein the intensity of the feedback stimulation signal is reduced. In a preferred embodiment the feedback stimulation signal is reduced by half, to avoid burning or skin irritation due to too great a current being passed from one electrode to a better connected electrode. In yet another embodiment the feedback stimulation signal may be blocked.

Accordingly, in one embodiment an interlock may be provided such that the means for providing a feedback signal upon the detection of EMG signals indicative of a muscular activity is prevented from so doing if the amplitude of the said frequency of the monitoring signal in signals received at said inputs is not indicative of a sufficiently good connection, e.g. is not below a preset threshold level of voltage sufficient to provide a set level of current, or wherein the intensity of the feedback signal is reduced if there is not a sufficiently good connection, e.g. if the amplitude of the said frequency of the monitoring signal in signals received at said inputs is not below a preset threshold level of voltage sufficient to provide a set level of current, e.g. if the amplitude of the said frequency of the monitoring signal in signals received at said inputs is not below a preset threshold level of voltage sufficient to provide a set level of current.

Thus, where electrodes are placed on the skin and a feedback stimulation signal is applied through them, the apparatus according to the invention can avoid the feedback signal being provided if the connection to the skin is not sufficiently good, and thus the risk of skin irritation or burning may be avoided.

Preferably, the apparatus comprises a said first electrode, a said second electrode and a said reference electrode, said monitoring signal is applied to said first electrode and to said second electrode and the amplitude of the frequency of the monitoring signal at said reference electrode is measured to determine the quality of the connection via the skin between the first electrode and the reference electrode and the quality of the connection via the skin between the second electrode and the reference electrode.

Suitably, said monitoring signal is applied at a voltage sufficient to produce a preset current between the first electrode and the reference electrode and between the second electrode and the reference electrode.

An advantage of the use of a monitoring signal of known frequency that is detected via analysis of received signals is that the monitoring may be carried out continuously, whilst EMG signals are simultaneously detected and evaluated.

An index indicative of the quality of the electrode connections as monitored over a period of time may be recorded, suitably providing a single figure which indicates to a user how good over the use period the connection has been. The index figure may for instance be generated by producing a numerical output indicative of the quality of connection at periodic intervals and averaging the values of said numerical output values over time.

In one aspect, the invention provides a novel approach to monitoring electrode connections, such as electrode connections to the skin of an individual. Accordingly, the present invention provides apparatus for receiving and monitoring electrical signals comprising respective inputs for receiving signals from at least a first electrode and a reference electrode, a Fourier transform analyser for extracting frequency content information from said signals, a source of a monitoring signal having a frequency, an output for use in applying said monitoring signal to a said electrode, and means for determining the amplitude of the said frequency of the monitoring signal in signals received at said inputs as determined by said Fourier transform analyser.

The Fourier transform analyser is preferably a DFT analyser, such as an FFT analyser. This can provide a power spectrum of the received signals in which the amplitude of the signal at the frequency of the monitoring signal can be determined.

In yet another aspect the invention relates to a method for ameliorating and/or treating undesired muscular activity, in particularly bruxism, by applying electrodes as described above to the skin above a facial muscle of said individual, preferably the masseter muscle or the temporalis muscle, applying a stimulating signal, should a bruxism event happen, and monitoring the connection between the electrodes and the skin. Accordingly, in a further aspect the invention relates to a method for monitoring activity of the temporal muscle and/or the masseter muscle, in particular activity due to teeth and/or jaw clenching, said method comprising the steps of:

measuring EMG signals from said electrode(s) when the electrodes are applied to the skin, applying a monitoring signal having a frequency to said at least first electrode, determining the received signal of said frequency of the monitoring signal in signals received, for monitoring the quality of the electrical connection between the electrodes and the skin, providing an electrical stimulation feedback signal upon the detection of EMG signals indicative of a muscular activity of the individual, wherein the feedback signal is modulated if the quality of the electrical connection between the electrodes is changed. Embodiments of this aspect is described above in relation to the apparatus.

Furthermore, the present invention provides a method for monitoring the electrode connection, wherein the incoming signals relating to the monitoring signals are analysed by a Fourier transform analyser. Accordingly, in another aspect, the invention relates to a method for monitoring electrode connections, by receiving and monitoring electrical signals from at least a first electrode and a reference electrode, extracting frequency content information from said signals and performing a Fourier transform analysis, applying said monitoring signal to a said electrode, and determining the amplitude of the said frequency of the monitoring signal in signals received as determined by said Fourier transform analyser. Embodiments of this aspect is described above in relation to the apparatus.

The invention will be further described and illustrated by reference to the accompanying drawings in which:

DETAILED DESCRIPTION OF THE DRAWINGS

Figure 2:
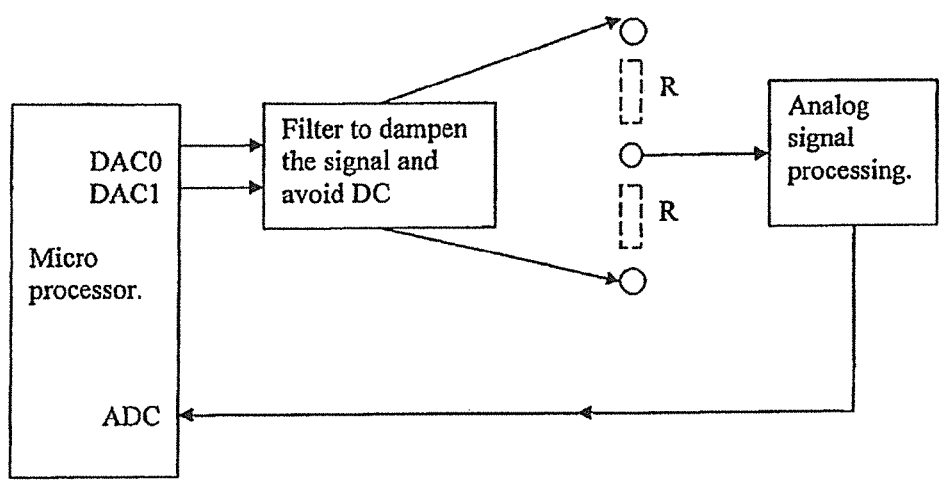
FIG. 2 is a block circuit diagram showing the components of the apparatus of FIG. 1 that are relevant to the electrode connection monitoring.

The circuitry shown in FIGS. 1 and 2 is that of apparatus for monitoring bruxism which is generally of the kind described in detail in WO 2004/087258. The apparatus has an electrode assembly comprising a first electrode 10, a second electrode 14 and a reference electrode 12 disposed between the first and second electrodes. The three electrodes are applied to the skin of a user above either the temporal muscle (musculus temporalis) or the masseter muscle (musculus masseteŋ. EMG signals received from the electrodes 10 and 14 are fed via an analog switch, switching between sending and receiving functions as discussed below, to an Instrumentation amplifier and then to a notch filter for removing ambient 50/60 Hz noise. After processing by a digital amplifier the signals are low pass filtered with a cut off nominally at 500 Hz which allows a significant amount of the frequency content of the monitoring signal at 610 Hz to pass. The resulting filtered signals are subjected to FFT analysis in a micro-processor to analyse their frequency content. The microprocessor further controls the switching of that analogue switch between receiving and sending states.

If there is found to be present a sufficient amplitude at one or more preset frequencies or within one or more preset frequency bands in the received EMG signals, it is considered that an episode of bruxism is occurring and an instruction is sent to the unit marked 'stimulator' to generate a stimulation signal, which is applied to the reference electrode. This gives the user a mild electric shock which is designed to be insufficient to wake them if they are sleeping. Current passes from the reference electrode to each of the first and second electrodes.

The micro-processor also outputs trigger signals to a first output 16 and to a second output 18 which connect respectively to first and second monitor signal generators DAC0 and DAC1 which convert the digital trigger signals to a 610 Hz sine wave monitoring signal. The monitoring signals are thereby applied alternately to the first and second electrodes via a filter to dampen the signal and to exclude a DC component (FIG. 2) at a voltage sufficient to achieve a preset current value. The voltage is therefore dependent on the resistance between the relevant electrodes (electrode 10 to reference 12 in the case of DAC0 and electrode 14 to reference 12 in the case of DAC1). As shown in FIG. 2, the monitor signals are picked up from the reference electrode and are fed to an analogue to digital converter and are analysed in the microprocessor as part of the FFT analysis of the EMG signals received from the first and second electrodes.

Sufficient of the applied 610 Hz signal passes the filters to be picked up in the EMG signals.

If the amplitude of the monitoring signal voltage applied to one (but not the other) of electrodes 10 and 14 to achieve the preset current is too high, implying a poor connection between the electrodes, the stimulation signal intensity is reduced, suitably by half, to avoid burning or skin irritation due to too great a current being passed from the reference electrode 12 to just the better connected one of the first and second electrodes 10, 14. If the amplitude of the monitoring signal is too high as received from both of the electrodes 10, 14, then the giving of the stimulation signal is blocked. This could be due to a poor connection either at both of electrodes 10 and 14, or just at the reference electrode. It can happen that one or both of the first and second electrodes becomes short circuited to the reference electrode, for instance if conductive gel becomes smeared over the skin between them. One will then detect too low an amplitude of the 610 Hz monitoring signal.

A log is written in the apparatus for the purposes of informing the user that one or both electrodes was not adequately connected during the session.

In a set-up phase of the use of the apparatus, the monitoring signals are used as a basis for confirming to the user (or not as appropriate) that an initial good connection of the electrode assembly has been made.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of.

The invention claimed is:

1. An apparatus comprising:
an electrode assembly comprising three electrodes: a first, a second and a reference electrode, mounted on a common substrate in a fixed spatial relationship one to another wherein said reference electrode lies approximately equidistant from said first and second electrodes, said electrode assembly adapted for being applied to the skin of an individual,
inputs for receiving signals from said electrodes,
wherein the apparatus is operative to measure EMG signals from said electrode(s) when the electrodes are applied to the skin and provide an electrical stimulation feedback signal to the reference electrode such that current passes from the reference electrode to each of the first and second electrodes during the stimulation upon the detection of EMG signals indicative of a muscular activity relating to bruxism of the individual, said apparatus further comprising:

a source of a monitoring signal having a frequency and outputs for use in applying said monitoring signal alternately to said first and second electrodes, wherein the apparatus is operative to determine an amplitude of the monitoring signal at said frequency at the input of said reference electrode, wherein the amplitude of the monitoring signal at said frequency at said reference electrode is measured to determine a quality of an electrical connection via the skin between the first electrode and the reference electrode and a quality of an electrical connection via the skin between the second electrode and the reference electrode, wherein current passes from each of the first and second electrodes to the reference electrode during the measuring of the amplitude of the monitoring signal, and wherein an intensity of the electrical stimulation feedback signal is modulated if the quality of the electrical connections between the electrodes is changed.

2. An apparatus as claimed in claim 1, comprising a Fourier transform analyser for extracting frequency content information from said received signals.

3. An apparatus as claimed in claim 2, wherein said apparatus is for measuring EMG signals from said electrodes when the electrodes are applied to the skin and the amplitude of the monitoring signal at said frequency in signals received at said inputs as determined by said Fourier transform analyser is measured for monitoring the quality of the electrical connection between the electrodes and the skin.

4. An apparatus as claimed in claim 1, wherein said apparatus is configured so that said monitoring signal is applied at a voltage sufficient to produce a preset current between the first electrode and the reference electrode and between the second electrode and the reference electrode.

5. An apparatus as claimed in claim 1, wherein the apparatus is operative to measure the amplitude of the received signals of at least one selected frequency other than the frequency of said monitoring signal.

6. An apparatus as claimed in claim 1, wherein said EMG signals indicative of the muscular activity are identified by measuring therein the amplitude of the received signals at one or more selected frequencies different from the frequency of the monitoring signal.

7. An apparatus as claimed in claim 1, wherein the intensity of the electrical stimulation feedback signal is reduced when the quality of the electrical connection is reduced.

8. An apparatus according to claim 1, wherein the intensity of the electrical stimulation feedback signal is reduced if the amplitude of the monitoring signal at said frequency, in signals received at said inputs, is not below a preset threshold level.

9. An apparatus as claimed in claim 1, wherein the intensity of the electrical stimulation feedback signal is reduced by half.

10. An apparatus as claimed in claim 1, wherein the intensity of the electrical stimulation feedback signal is modulated without turning off the feedback signal.

11. A method for monitoring muscular activity of a temporal muscle and a masseter muscle of an individual, wherein the muscular activity is relating to bruxism of the individual, said method comprising the steps of:

providing an apparatus as defined in claim 1 comprising a first, a second, and a reference electrode, measuring EMG signals from said electrodes when the electrodes are applied to the skin, applying a monitoring signal alternately to said first and second electrodes, said monitoring signal having a frequency, wherein current passes from each of said first and second electrodes to the reference electrode during the applying;

determining an amplitude of the monitoring signal at said frequency at the input of said reference electrode, thereby determining a quality of an electrical connection via the skin between the first electrodes and the reference electrode, and a quality of the connection via the skin between the second electrode and the reference electrode, and providing an electrical stimulation feedback signal to the reference electrode upon the detection of EMG signals indicative of a muscular activity relating to bruxism of the individual, the electrical stimulation feedback signal provided such that current passes from the reference electrode to each of the first and second electrodes during the stimulation, wherein an intensity of the electrical stimulation feedback signal is modulated if the quality of the electrical connections between the electrodes is changed.

12. The method as claimed in claim 11, wherein the amplitude of the monitoring signal is determined by determining the amplitude of the monitoring signal at said frequency, in signals received.

13. The method as claimed in claim 11, wherein said monitoring signal is applied at a voltage sufficient to produce a preset current between the first electrode and the reference electrode and between the second electrode and the reference electrode.

14. The method as claimed in claim 11, comprising extracting frequency content information from said received signals and performing a Fourier transform analysis.

15. The method as claimed in claim 11, comprising the further step of receiving signals from said first electrode, from said second electrode and from said reference electrode.

16. The method as claimed in claim 15, wherein the respective electrodes are connected.

17. The method as claimed claim 11, further comprising the step of measuring the amplitude within the received signals of at least one selected frequency other than the frequency of said monitoring signal.

18. The method as claimed in claim 11, wherein said activity is an episode of bruxism.

19. The method as claimed in claim 11, wherein the step of measuring said EMG signals comprises measuring therein the amplitude of said signals at one or more selected frequencies different from the frequency of the monitoring signal.

20. The method as claimed in claim 11, wherein the intensity of the electrical stimulation feedback signal is reduced, when the quality of the electrical connection is reduced.

21. The method according to claim 11, wherein the intensity of the electrical stimulation feedback signal is reduced if the amplitude of the monitoring signal at said frequency, in signals received is not below a preset threshold level.

22. The method as claimed in claim 11, wherein the intensity of the electrical stimulation feedback signal is reduced by half.

23. The method as claimed in claim 11, wherein the intensity of the electrical stimulation feedback signal is modulated without turning off the feedback signal.

* * * * *